United States Patent [19]

Ureda et al.

[11] Patent Number: 5,332,845

[45] Date of Patent: Jul. 26, 1994

[54] PHOSPHORYLATING REAGENTS

[75] Inventors: Michael S. Ureda, Alamo; Thomas Horn, Berkeley, both of Calif.

[73] Assignee: Chiron Corporation, Emeryville, Calif.

[21] Appl. No.: 23,932

[22] Filed: Feb. 26, 1993

Related U.S. Application Data

[60] Division of Ser. No. 87,158, Aug. 18, 1987, Pat. No. 5,260,760, which is a continuation-in-part of Ser. No. 891,789, Jul. 30, 1986, abandoned, which is a continuation-in-part of Ser. No. 845,290, Mar. 28, 1986, abandoned, which is a continuation-in-part of Ser. No. 717,206, Mar. 28, 1985, abandoned.

[30] Foreign Application Priority Data

Mar. 27, 1986 [CA] Canada ............................. 504420
Mar. 27, 1986 [EP] European Pat. Off. ......... 861042505
Mar. 27, 1986 [JP] Japan .............................. 61-067385

[51] Int. Cl.$^5$ .......................... C07F 9/09; C07F 9/141
[52] U.S. Cl. .................................... 552/105; 544/157
[58] Field of Search ............... 536/25.3, 25.33, 25.34, 536/26.1, 55.3; 549/214, 218; 558/168, 175, 178, 184, 169, 202; 435/15; 544/106, 157; 552/105

[56] References Cited

U.S. PATENT DOCUMENTS 4,415,732 11/1983 Caruthers et al. ................. 536/26.5
4,692,542 9/1987 Tesser et al. ....................... 558/184
5,039,796 8/1991 Engels et al. ...................... 536/25.3

FOREIGN PATENT DOCUMENTS 0131993 1/1985 European Pat. Off. .

OTHER PUBLICATIONS

Claesen et al. Recl. Trav. Chim. 104: 119-122, 1985.
Fisher et al. Nucl. Acids Res. 11(5): 1589-1599, 1983.
Beaucage et al., Tetrahedron Letters, 22(20): 1859-1862, 1981.
Froehler et al., Tetrahedron Letters, 24(31): 3171-3174, 1983.
Froehler et al., Nucleic Acids Res., 14(13): 5399-5407, 1986.
Froehler et al., Nucleic Acids Research, 11(22): 8031-8036, 1983.
Horn et al., Nucleosides & Nucleotides, 5(1&2): 335-340, 1987.
Horn et al., Tetrahedron Letters, 27(39): 4705-4708, 1986.
Horn et al., DNA, 5(5): 421-426, 1986.
Jablonski et al. Nucleic Acids Research 14(15): 6115-6128, 1986.
McBride et al., Tetrahedron Letters, 24(3): 245-248, 1983.
Perich et al., Tetrahedron Letters, 28(1): 101-102, 1987.
Smith, Synthesis pp. 15-24, Dec., 1983.
Sonveaux, Bioorganic Chemistry, 14: 274-325, 1986.
Uhlmann et al., Tetrahedron Letters, 27(9): 1023-1026, 1986.
Warner et al., DNA 3(5): 401-411, 1984.

*Primary Examiner*—Johnnie R. Brown
*Assistant Examiner*—Gary L. Kunz
*Attorney, Agent, or Firm*—Dianne E. Reed; Kenneth M. Goldman; Robert P. Blackburn

[57] ABSTRACT

Novel phosphorylating reagents are provided which are useful in DNA synthesis and purification procedures. The reagents are substituted phosphines which are particularly useful in the phosphorylation of nucleoside and solid supported oligonucleotides at the 5'-hydroxyl position. Phosphorylation using these reagents is easily and accurately monitored colorimetrically.

20 Claims, No Drawings

PHOSPHORYLATING REAGENTS

CROSS-REFERENCE TO RELATED APPLICATIONS

This application is a division of application Ser. No. 07/087,158 field Aug. 18, 1987 issued as U.S. Pat. No. 5,260,760, which is a continuation-in-part of Ser. No. 06/891,789 filed Jul. 30, 1986, now abandoned which is a continuation-in-part of Ser. No. 06/845,290 filed Mar. 28, 1986, now abandoned, which is a continuation-in-part of Ser. No. 06/717,206 filed Mar. 28, 1985, now abandoned.

DESCRIPTION

1. Technical Field

The invention relates to chemical phosphorylation reagents and more particularly relates to chemical phosphorylation reagents useful in DNA synthesis and purification.

2. Background

With the advent of hybrid DNA technology and the explosion in the ability to isolate, purify, and assay a wide variety of natural products, both polypeptides and nucleic acids, there is an increasing need for rapid and efficient methods of preparing and purifying oligomers of amino acids and nucleic acids.

With nucleic acids, it is typically necessary to synthesize sequences for use as linkers, adapters, synthetic genes and synthetic regulatory sequences, as well as for use as probes, primers, and the like. Many procedures have been developed for producing oligomers of nucleotides. These procedures for the most part rely on initial attachment of a first nucleotide to a solid support by a selectively clearable linkage, followed by sequential addition of subsequent nucleotide units, with each addition involving a number of chemical reactions.

The two primary methods of oligonucleotide synthesis which are well-established in the art are the so-called "phosphotriester" and "phosphoramidite" methods (described at some length in the references cited below). In the most prevalent schemes for both methods, the oligonucleotide chain grows by nucleophilic attack of the 5'-OH of the immobilized oligomer on an activated 3'-phosphate or phosphoramidite function of a soluble 5'-protected nucleotide building block. Other key steps include the acid deprotection of the 5'-O-(4,4'-dimethoxytrityl) group (DMTr) in the phosphotriester method, and, in the phosphoramidite process, the oxidation of the phosphite triester to the phosphate triester.

Other methods of oligonucleotide synthesis are also known, including 5' to 3' syntheses which use a cyanoethyl phosphate protecting group (De Napoli et al., *Gazz. Chim. Ital.* 114:65 (1984); Rosenthal et al., *Tetrahedron Lett.* 24:1691 (1983); Belagaje and Brush, *Nucleic Acids Res.* 10:6295 (1977)) and solution phase 5' to 3' syntheses (e.g., Hayatsu and Khorana, *J. Amer. Chem. Soc.* 89:3880 (1967); Gait and Sheppard, *Nucleic Acids Res.* 4:1135 (1977); Cramer and Koster, *Angew. Chem. Int. Ed. Eng.* 7:473 (1968); and Blackburn et al., *J. Chem. Soc. C*, 2438 (1967)).

After completion of oligonucleotide synthesis and deprotection of the product, the free 5'-OH group of the oligonucleotide must be phosphorylated or phosphitylated for use in most biological processes. Also, phosphorylation or phosphitylation on the 3'-OH function is typically necessary to generate oligonucleotides in a form that can be purified, stored and/or commercialized. See Sonveaux, *Bioorganic Chem.* 14:274,294 (1986). The present invention is directed to compounds which are useful in phosphorylating and phosphitylating both 3' and 5' hydroxyl moieties.

5'-phosphorylation is generally carried out with T4 polynucleotide kinase and ATP, a reaction that is not particularly reliable or efficient. Several methods for chemical 5'-phosphorylation are also known, including that described in Nadeau et al, *Biochemistry* 23:6153–6159 (1984), van der Marel et al., *Tetrahedron Lett.* 2.2.:1463–1466 (1981), Himmelsbach and Pfleiderer, *Tetrahedron Lett.* 23:4793–4796 (1982), Marugg et al., *Nucleic Acids Res.* 12:8639–8651 (1984), and Kondo et al., *Nucleic Acids Research Symposium Series* 16:161–164 (1985). However, most of these methods involve the use of unstable reagents or require extensive modification of standard deprotection and purification procedures. Similar problems have been found with monofunctional and bifunctional 3'-phosphorylating reagents (see Sonveaux, supra, at 297).

The present invention is directed to novel phosphorylating reagents which overcome the limitations of current phosphorylation procedures. As used herein, the term "phosphorylating reagent" encompasses compounds which can phosphorylate a hydroxyl group directly as well as phosphitylating agents which, when coupled with a subsequent oxidation step, can phosphorylate hydroxyl groups indirectly, i.e., in a two-step reaction sequence. The phosphorylating reagents disclosed herein are also useful in the method of the parent application hereto, U.S. Ser. No. 891,789, which is directed to a method of synthesizing and purifying oligonucleotides substantially free of erroneous sequences. The disclosure of that application is hereby expressly incorporated by reference in its entirety.

The reagents of the present invention, especially the phosphitylating reagents as will be 5 described, are advantageous in that they are easily accommodated by currently available DNA synthesis machines. Also, the phosphorus blocking groups designated herein as Y, Y' or Y" are easily removed during deprotection of the completed oligonucleotide and do not require any additional deprotection steps. Most importantly, the reagents disclosed herein provide for rapid and accurate online monitoring of oligonucleotide synthesis. That is, the present compounds yield a leaving group upon deprotection of the completed oligonucleotide which is readily observable.

DESCRIPTION OF THE PRIOR ART

In addition to the art cited above, Matteucci and Caruthers, *J. Am. Chem. Soc.* 103:3185–3191 (1981), describe the use of phosphorchloridites in the preparation of oligonucleotides. Beaucage and Caruthers, *Tetrahedron Lett.* 22:1859–1862 (1981) and U.S. Pat. No. 4,415,732 describe the use of phosphoramidites in the preparation of oligonucleotides. Smith, *ABL* 15–24 (Dec. 1983), describes automated solid phase oligodeoxyribonucleotide synthesis. See also the references cited therein, and Warner et al., *DNA* 3:401–411 (1984), whose disclosure is incorporated herein by reference.

Fisher and Caruthers, *Nucl. Acids Res.* 11(5):1589–1599 (1983), describe a procedure for monitoring the progress of a deoxynucleotide synthesis. That procedure involves monitoring the release of various triarylmethyl groups during synthesis, each of which is "color coded," i.e., are differently colored in acid solution.

Amidine protection of adenosine has been described by McBride and Caruthers, *Tetrahedron Lett.* 24:245 (1983) and Froehler and Matteucci, *Nucl. Acids Res.* 11:8031 (1983). Other blocking groups are described in co-pending application Ser. No. 891,789, now abandoned, the parent application hereto.

Horn and Urdea, *DNA* 5(5):421-425 (1986) describe phosphorylation of solid-supported DNA fragments using bis(cyanoethoxy)-N,N-diisopropyl-aminophosphine.

DISCLOSURE OF THE INVENTION

In one aspect of the invention, the invention encompasses phosphitylating reagents having the structure I

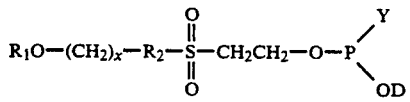

wherein: $R_1$ may be virtually any group whose release upon phosphorylation and nucleotide deprotection can be monitored, e.g., colorimetrically. $R_1$ is preferably a compound having the formula RR'R''C- wherein the R, R' and R'' are independently selected from the group consisting of

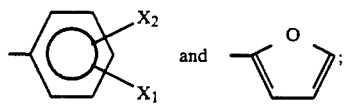

wherein the $X_1$ and $X_2$ may be ortho, meta or para to each other and are typically hydrogen, lower alkyl, lower alkoxy, halogen, nitro, phenyl, sulfonate, or amines substituted with from 0 to 2 lower alkyl or lower alkoxy substituents. $X_1$ and $X_2$ may also be part of a polycyclic aromatic system having typically from one to five rings, such as phenyl, naphthyl or the like. In the latter case, $X_1$ and $X_2$ are carbon atoms which are para to each other in the higher conjugated aromatic structure, and the rings may be unsubstituted or substituted with one or more of the aforementioned substituents. $R_2$ is selected from the group consisting of methylene optionally mono- or disubstituted with lower alkyl and phenyl optionally substituted with lower alkyl or nitro. Y is selected from the group consisting of amino substituted with from 0 to 2 lower alkyl groups, halogen trialkylsilyl of from 3 to 12 carbon atoms, and heterocyclic moieties typically having a total of from 1 to 3, usually 1-2, heteroannular members and from 1 to 3 rings, and x is an integer in the range of 1 and 50 inclusive. D is selected from the group consisting of (i) the structure II:

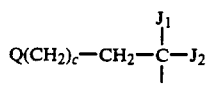

in which $J_1$, and $J_2$ are independently selected from the group consisting of hydrogen and alkyl of 1 to 3 carbon atoms, c is 0 or 1, and Q is typically selected from the group consisting of hydrogen, alkyl of from 1 to 9 carbon atoms, nitro, alkylsulfonyl (generally lower alkylsulfonyl), arylsulfonyl, cyano, p-nitrophenyl, alkylthio (generally lower alkylthio), arylthio, trihalomethyl, and (ii)phenyl, beta-naphthyl, 9-fluorenyl and 2-anthraquinonyl.

The invention also encompasses phosphitylating reagents given by the structure III and phosphorylating reagents given by the structure IV:

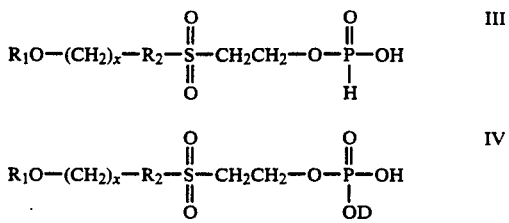

wherein $R_1$, $R_2$, D and x are as given above for the reagents of Formula I.

The reagents of the invention can be used either to phosphitylate hydroxyl-containing compounds to give phosphite triesters (i.e., using the reagents of Formulae I and III) or to phosphorylate hydroxyl-containing compounds to give phosphate triesters (i.e., using the reagent of Formula IV).

Where a phosphoramidite according to formula I is used as a phosphitylating agent, an activating agent is typically necessary as well. Suitable activating agents are described, for example, in Froehler and Matteucci, *Tetrahedron Lett.*, 24:3171 (1983) and Beaucage and Caruthers (1981), supra. Where phosphitylation is effected using the reagent of Formula III, or where phosphorylation is carried out using the reagent of Formula IV, a condensing agent as described in the literature (e.g., Sonveaux, supra, or Froehler and Matteucci, *Tetrahedron Lett.* (1983), supra), is to be used. As noted in U.S. patent application Ser. No. 891,789, the parent application hereto, preferred condensing agents are activated aryl sulfonic acid compounds such as mesitylene sulfonyl-3-nitro-1,2,3-triazole, or mesitylenesulfonyl chloride and H-methylimidazole.

In the case of the phosphitylating reagents, it is generally desirable to oxidize the resulting phosphite triesters to give the corresponding phosphate triesters and phosphate salts.

In another aspect, then, the invention encompasses a method of phosphorylating the 5'-hydroxyl group of nucleosides and oligonucleotide chains via the aforementioned methods. Such a method is useful subsequent to synthesis of an oligonucleotide chain, so that the completed sequence will be 5'-phosphorylated for further use. The reagents are also useful in providing hydroxyl blocking groups—i.e. phosphite or phosphate triesters—during DNA synthesis.

Modes of Carrying Out the Invention

1. Definitions

By oligonucleitide" is meant a nucleotide chain having from about 2 to about 100 component nucleotide monomers.

The terms "phosphorylating conditions" or "phosphitylating conditions" as used herein are intended to mean reaction conditions suitable for substantially complete phosphorylation or phosphitylation, respectively, of a hydroxyl-containing compound as will be described.

By "phosphorylating reagents" as used herein are meant compounds which include a phosphorous atom in the +5 oxidation state and, upon reaction with hydroxyl-containing compounds, yield a phosphate triester.

By "phosphitylating reagents" as used herein are meant compounds which include a phosphorous atom in the +3 oxidation state and, upon reaction with hydroxyl-containing compounds, yield a phosphite triester. As phosphitylation coupled with a subsequent oxidation step is equivalent to a two-step phosphorylation, phosphitylating reagents may sometimes be referred to herein as "phosphorylating reagents."

"Lower alkyl" and "lower alkoxy" designate alkyl and alkoxy groups, respectively, having from 1 to 6 carbon atoms.

2. Structure of the Novel Reagents

The reagents of the present invention are the phosphorylating agents defined by Formulae I-IV above.

In general, the $R_1$, $R_2$, D, and Y substituents are as given above, and x is typically in the range of 1 and 50 inclusive. In a preferred embodiment:

(1) The integer "x" is in the range of 1 and 8 inclusive.
(2) $R_1$ is 4,4'-dimethoxytrityl.
(3) Y is an amine substituent of the formula $-NT^1T^2$, where $T^1$ and $T^2$ may be the same or different and may be hydrocarbon or have from 0 to 5, usually 0 to 4 heteroatoms, primarily oxygen as oxy, sulfur as thio, or nitrogen as amino, particularly tert-amino, $NO_2$, or cyano. The two T's may be taken together to form a mono- or polyheterocyclic ring having a total of from 1 to 3, usually 1 to 2 heteroannular members and from 1 to 3 rings. Usually, the two T's will have a total of from 2 to 20, more usually 2 to 16 carbon atoms, where the T's may be aliphatic (including alicyclic), particularly saturated aliphatic, monovalent, or, when taken together, divalent radicals defining substituted or unsubstituted heterocyclic rings. The amines defined by Y include a wide variety of saturated secondary amines such as dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperazine and similar saturated monocyclic nitrogen heterocycles (U.S. Pat. No. 4,415,732).

Specific groups reported for use as $-NT^1T^2$ are as follows:

| | |
|---|---|
| N-pyrrolidino | Beaucage, Tetrahedron Lett. 25:375 (1984), Schwarz and Pfleiderer, ibid 25:5513 (1984) |
| $N = \chi^1$ $\chi^1$ - alkylene of 4–12 carbon atoms, p-bis-dimethylene-cyclohexane, bis-diethylene sulfide and methylamino | |
| $N\chi^1$; $T^1$, $T^2$—Me, iPr | McBride and Caruthers, ibid 24:245 (1983) |
| $\chi^1$ - bis-diethyleneoxy, $\alpha,\alpha,\alpha',\alpha'$-tetramethylpentamethylene | |
| nitroimidazole, tetrazole | Matteucci and Caruthers, J. Am. Chem. Soc. 103:3185 (1981) |

Illustrative groups include: N-pyrrolidino, N-piperidino, 1-methyl-N-piperazino, N-hexahydroazipino, N-octahydroazonino, N-azacyclotridecano, N-3-azabicyclo(3.2.2.)nonano, thiomorpholino, N,N-diethylamino, N,N-dimethylamino, N,N-diisopropylamino, piperidino, 2,2,6,6-tetramethyl-N-piperidino.

Y may also be halo, e.g., chloro (Letsinger and Lunsford, J. Am. Chem. Soc. (1976) 98:3655; Matteucci and Caruters, supra) or an ammonium oxy salt, particularly trialkylammonium of from 3 to 12 carbon atoms.

(4) For the most part as noted above, D is illustrated by Formula II wherein $J_1$, $J_2$ and $J_3$ are independently selected from the group consisting of hydrogen and alkyl of 1 to 3 carbon atoms, c is 0 or 1, and Q is typically selected from the group consisting of hydrogen, alkyl of from 1 to 9 carbon atoms, nitro, generally lower alkylsulfonyl, alkylsulfonyl, arylsulfonyl, cyano, p-nitrophenyl, alkylthio, generally lower alkylthio, arylthio, trihalomethyl, and (ii)phenyl, beta-naphthyl, 9-fluorenyl and 2-anthraquinonyl.

Specific groups reported for use as D are as follows:

| | |
|---|---|
| alkyl | Beaucage and Caruthers, Tetrahedron Lett. 22:1859 (1981) |
| $NCCH_2C(Me)_{0-2}(H_{2-0})-$ | Koster, Nucleic Acids Res. 12:4539 (1984); Marugg et al., Rec. trav. Chim. Pay-Bays 103:97-8 (1984); Van Boom et al., Nucleic Acids Res. 12:8639 (1984) |
| $p-\phi_2NOCH_2CH_2-$ | Schwarz and Pfleiderer, Tetrahedron Lett. 25:5513 (1984) |
| $MeSO_2CH_2CH_2-$ | Claesen et al., ibid 25:1307 (1984) |
| $(halo)_3CC(Me)_{0-2}(H)_{0-2}-$ | Takaku et al., Chemistry Letters 1984:1267; Letsinger et al., Tetrahedron 40:137 (1984) |
| $\phi(CH_2)_{0-1}S(O)_{0-2}(CH_2)_2$ | Balgobin et al., Tetrahedron Lett. 22:1915 (1981); Agarwal et al., J. Am. Chem. Soc. 98:1065 (1976); Felder et al., Tetrahedron Lett. 25:3967 (1984) |
| $(\chi)_{0-2}OCH_2-$, 2-naphthyl-$CH_2-$, 9-fluorenyl-$CH_2-$, 2-anthraquinonyl-$CH_2-$ | Caruthers et al., Nucleic Acids Res. Sym. Ser. 7:215; (1980); Christodonlon & Reese, Tetrahedron Lett. 24:1951 (1983); Kwiatkowski et al., Abstract, Conf. on Syn. Oligonucleotides in Molecular Biology, Uppsala, Sweden Conf. 16–20 #64 (1982); Balgobin, ibid |
| $\chi CH_2CH_2-$ | Uhlmann et al., Tetrahedron Lett. 21:1181 (1980); Schulz and Pfleiderer, ibid 24:3582 (1983); Beite and Pfleiderer, ibid 25:1975 (1984) |
| $MeCOCH(Me)-$ | Ramirez et al., Tetrahedron 39:2157 (1983) |
| $\phi_3CO(Cl)$ | Vasseur et al., Tetrahedron Lett. 24:2573 (1983) |

$\chi$ may be hydrogen or any non-interfering stable substituent, neutral or polar, electron donating or withdrawing, generally being of 1 to 10, usually 1 to 6 atoms and generally of from 0 to 7 carbon atoms, and may be an aliphatic, alicyclic, aromatic or heterocyclic group, generally aliphatically saturated, halohydrocarbon, e.g., trifluoromethyl, halo, thioether, oxyether, ester, amide, nitro, cyano, sulfone, amino, azo, etc.

3. Synthesis of the Phosphorylating Reagents

The phosphitylating reagent given by Formula I may be synthesized by a method analogous to that described in Horn and Urdea, *Tetrahedron Lett.* 27(39):4705–4708 (1986), the disclosure of which is hereby incorporated by reference.

A compound of formula

V is initially provided, wherein: (1) in a first, preferred embodiment, R' is halogen, preferably chlorine, R" is Y as defined above, and R'" is —OD as defined above; (2) in a second embodiment, R' and R" are both Y and may or may not be identical, and R'" is —OD; and (3) in a third, alternative, embodiment, R' R" and R'" are all halogen, preferably clorine. This compound is reacted with an alcohol of Formula VI.

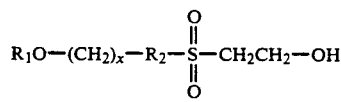
VI under an inert atmosphere and at a relatively low temperature, preferably about 0° C., to give a structure in which either a halogen substituent (embodiment (1)) or a "Y" substituent (embodiments (2) and (3)) has been replaced by

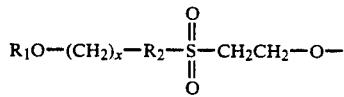
VII to give the phosphitylating agent of Formula I. (In the case of alternative embodiment (3), the resulting compound is caused to couple to a substituent "OD", followed by reaction with an amine moiety "Y" according to synthetic methods known in the art, to yield the structure of Formula I.)

The phosphitylating reagent given by Formula III is prepared by condensation of the alcohol of Formula V with phosphorous acid or an alkylated analog thereof, in the presence of an activating agent such as tosyl chloride.

The phosphorylating reagent of Formula IV is prepared in a manner analogous to that described above for the reagent of Formula I, except that the starting material is

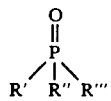
VIII wherein: (1) in a first, preferred embodiment, R' is halogen, preferably chlorine, R" is —OD as defined above, and R'" is —OH; (2) in a second embodiment, R' and R" are both halogen, preferably chlorine, and R'" is —OD; and (3) in a third, alternative embodiment, R', R" and R'" are all halogen, preferably chlorine. In embodiments (2) and (3), an additional, hydrolysis, step is required, while in embodiment (3) specifically, still a further step is required to add the "OD" substituent using synthetic methods known in the art.

Isolation of the product is done via precipitation as the barium or triethylamine salt.

All of these reactions are preferably carried out neat in order to facilitate homogeneity and to avoid problems with solubility. If desired, however, any suitable inert solvent may be used, providing that all reagents involved are substantially soluble therein.

4. Phosphitylation and Phosphorylation Using the Novel Reagents

In general, the reagents disclosed herein are useful in converting free hydroxyl groups to phosphite and phosphate triesters. In a preferred embodiment, the free hydroxyl group so converted is the 5'-OH of a nucleoside or the 5'-OH of an oligonucleotide chain. The reaction proceeds according to Scheme I:

Scheme I

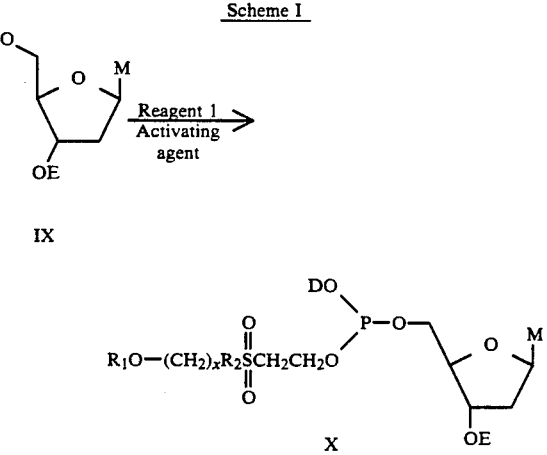

In Scheme I, the substituent "M" is a purine or pyrimidine base, which may be protected with amine protecting groups as disclosed in the parent application hereto. "E" is hydrogen, a suitable 3'-OH protecting group, or a continuing oligonucleotide chain.

Typically, the reaction conditions for the phosphorylation reaction of Scheme I are the same as those used in known methods of DNA synthesis, e.g., in the phosphoramidite (see Beaucage and Caruthers, *Tetrahedron Lett.* (1981), supra).

After conversion of the nucleoside or oligonucleotide chain to the phosphite triester given by structure X, oxidation to the corresponding phosphate triester (compound XI; Scheme II) may be effected using standard techniques, e.g., treatment with aqueous iodine or peroxide in a suitable, preferably slightly polar organic solvent such as tetrahydrofuran (THF). See, e.g., Horn and Urdea, *DNA*, supra.

Scheme II

X ⟶

-continued
Scheme II

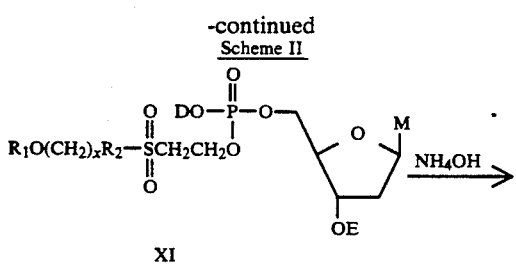

Release of the $R_1$ group is easily monitored, visually or colorimetrically, and thus allows for simple and accurate monitoring of the overall phosphorylation procedure.

As illustrated by Scheme II, the base-labile phosphate triester may be converted to phosphate salt XII by treatment with a deprotection agent, e.g. ammonium hydroxide. This step may proceed concurrently with release of the oligonucleotide chain from the solid support where the linkage to the solid support is a baselabile one.

Although phosphitylation and subsequent oxidation and deprotection steps (Scheme II) can be carried out in solution, it is preferred that the oligonucleotide substrate be bound to a solid support. A wide variety of supports may be used, such as silica, Porasil C, polystyrene, controlled pore glass (CPG), kieselguhr, poly(-dimethylacrylamide), poly(acrylmorpholide), polystyrene grafted onto poly(tetrafluoroethylene), cellulose, Sephadex LH-20, Fractosil 500, etc. References of interest include: Sonveaux, supra; Matteucci and Caruthers, supra, Chow et al., *Nucleic Acids Res.* (1981) 9:2807; Felder et al., *Tetrahedron Lett.* (1984) 25:3967; Gough et al., ibid (1981) 22:4177; Gait et al., *Nucleic Acids Res.* (1982) 10:6243; Belagaje and Brush, ibid (1982) 10:6295; Gait and Sheppard, ibid (1977) 4:4391; Miyoshi and Itakura, *Tetrahedron Lett.* (1978) 38:3635; Potapov et al., *Nucleic Acids Res.* (1979) 6:2041; Schwyzer et al., *Helv. Chim. Acta* (1984) 57:1316; Chollet et al., ibid (1984) 67:1356; Ito et al., *Nucleic Acids Res.* (1982) 10:1755; Efimov et al., ibid (1983) 11:8369; Crea and Horn, ibid (1980) 8:2331; Horn et al., *Nucleic Acids Res. Sym. Ser.* (1980) 7:225; Tragein et al., *Tetrahedron Lett.* (1983) 24:1691; Koster et al., *Tetrahedron* (1984) 40:103; Gough et al., *Tetrahedron Lett.* (1983) 24:5321; Koster et al., ibid (1972) 16:1527; Koster and Heyns, ibid (1972) 16:1531; Dembek et al., *J. Am. Chem. Soc.* (1981) 103:706; Caruthers et al., *Genetic Engineering: Principles and Methods*, eds. Setlow and Hollaender, Vol. 4, 1982, pp. 1-12, Plenum Press. N.Y.

Phosphitylation using the reagent of Formula III proceeds in a similar manner (see Froehler and Matteucci, supra), yielding

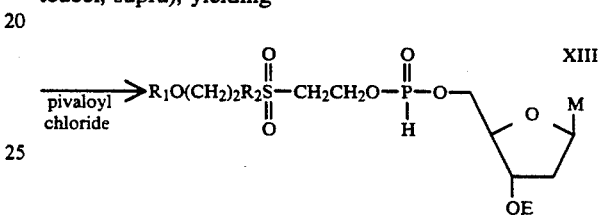

This compound may then be oxidized and deprotected as described above.

Phosphorylation using the reagent of Formula IV proceeds according to Scheme III and may be deprotected to the phosphate as described.

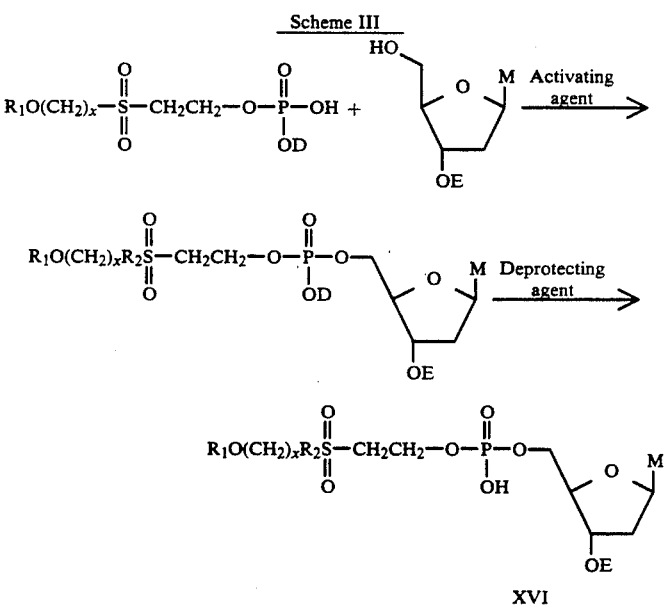

As described in the parent application hereto, depending on the nature of the support, different functionalities will serve as anchors. For silicon-containing supports, such as silica and glass, substituted alkyl or aryl silyl compounds will be employed to form a siloxane or siloximine linkage. With organic polymers, ethers, esters, amines, amides, sulfides, sulfones, phosphates may find use. For aryl groups, such as polystyrene, halomethylation can be used for functionalization, where the halo group may then be substituted by oxy, thio (which may be oxidized to sulfone), amino, phospho (as phosphine, phosphite or phosphate), silyl or the like. With a diatomaceous earth, e.g., kieselguhr, activation may be effected by treatment with a polyacrylic acid derivative followed by reaction with amino groups to form amine bonds. Polysaccharides may be functionalized with inorganic esters, e.g., phosphate, where the other oxygen serves to link the chain. With polyacrylic acid derivatives, the carboxyl or side chain functionality, e.g., N-hydroxethyl acrylamide, may be used in conventional ways for joining the linking group.

The linking group or chain will vary widely as to length, functionalities and manner of linking the first nucleotide. For extending chains, functionalities may include silyl groups, ether groups, amino groups, amide functionalities or the like, where bifunctional reagents are employed, such as diamines and dibasic acids, amino acids, saccharides, silanes, etc.

A number of supports and linking groups which have been reported in the literature are shown in the following Table.

age. The blocking groups are selected so as not to interfere with enzymatic degradation of a sequence lacking the terminal blocking group. At completion, the capping group is removed, blocking groups which interfere with enzymatic degradation are removed, and incomplete sequences lacking the terminal blocking group are degraded enzymatically. The oligomers may be retained on the support or removed prior to enzymatic degradation of the incomplete sequences. The completed correct sequences are then isolated substantially free of sequences having errors.

Thus, the method provides for selective, enzymatic removal of error-containing or incomplete oligonucleotides. This is achieved by employing terminal blocking functionalities which inhibit an exohydrolase from acting on a complete sequence, while the exohydrolase is capable of hydrolyzing an unblocked incomplete sequence. The method also employs capping functionalities which terminate sequences that have not undergone the next stage in the sequential addition, and prior to capping, retain the reactive free terminal (5'-OH) functionality. Thus, failure sequences terminate at the time of failure and are not continued.

TABLE

| Support[1] | Linking chain[2] | Terminal group[3] | Reference |
| --- | --- | --- | --- |
| Silica | $Si(CH_2)_3NHCO(CH_2)_2CO-$ | DMT-nucleoside | Mateucci & Caruthers, (1980), supra |
| Silica | Si-(5' att) | 3'Ac-Thymidine | Koster, Tetrahedron Lett. (1972), 16:1527 |
| Silica | $SiOC(O_2)O-$ (5' att) | Ac-nucleoside | Ibid. |
| CPG | $LCAA-CO(CH_2)CO-$ | $2'$-$o$-$O_2NOCH_2$, $5'DMT$-ribonucleoside | Gough et al., Ibid (1981) 22:4177 |
| CPG | $SiOSi(OEt)_2(CH_2)_3NHCO(CH_2)_2CO-$ | DMT-nucleoside | Koster et al., Tetrahedron (1984) 40:103 |
| CPG | $LCAA-CO(CH_2)_2CO-$ (5' att) | 2'-OCO-ribonucleoside | Gough et al., Tetrahedron Lett. (1983) 24:5321 |
| Porasil C | $Si(CH_2)_3NHCO(CH_2)_2CO-$ | DMT-nucleoside | Chow et al., Nucleic Acids Res. (1981) 9:2807 |
| Kieselguhr - PDMA | $N(Me)CH_2CONH(CH_2)_2-$ $(COCH_2NH)_2CO(CH_2)_2CO$ | DMT-nucleoside | Gait et al., Ibid (1982) 10:6243 |
| Polystyrene | $CH_2SO_2(CH_2)_2OP(ClOO))_2$ | DMT-nucleoside | Felder et al., Tetrahedron Lett. (1984) 25:3967 |
| Polystyrene | $CH_2OOC(O)(MeOO)O-$ (5' att) | nucleoside-(3'-C10-phosphate) | Belagaje & Brush, Nucleic Acids Res. (1982) 10:6295 |
| Sephadex LH-20 | $OPO_2$ (5' att) | ribonucleoside | Koster & Heyns, Tetrahedron Lett. (1972) 16:1531 |
| Polyacrylamide | $CONH(CH_2)_2NHCO(CH_2)_2CO-$ | DMT-nucleoside | Dembek et al., J. Am. Chem. Soc. (1981) 103:706 |
| Fractosil 500 | $(CH_2)_3NH(CH_2)_2CO-$ | DMT-nucleoside | Caruthers et al., Genetic Engineering (1982) 4:12 |
| Polyacrylmorpholide | $(CH_2)_nNH-$ | ribo- or deoxyribonucleoside | S. Pochet et al., Tetradron Lett. (1985) 26:627 |
| Silica | $(CH_2)_nNH-$ | ribo- or deoxyribonucleoside | S. Pochet et al., supra |
| CPG(LCAA) | $(CH_2)_nNH-$ | ribo- or deoxyribonucleoside | S. Pochet et al., supra |

[1]CPG - controlled pore glass/PDMA - polydimethylacrylamide
[2]O - phenyl/Me - methyl/Et - ethyl/LCAA - long chain alkyl amino/att - attachment
[3]DMT - p,p'-dimethoxytrityl/Ac - acetyl/O - phenyl nucleoside intends deoxyribonucleoside/groups indicate O-protective groups/3' nucleoside attachment, unless otherwise indicated 5. Use in Purification Method of U.S. Ser. No. 891,789

Briefly, the method described in the parent application hereto involves synthesis of oligonucleotide chains in such a way that contamination with erroneous sequences is minimized. The oligomerization occurs while the growing chain remains bound to an insoluble support. After each stage, failure sequences are capped and the next monomer added until the sequence is complete. Protective groups on the individual monomers, terminal blocking groups, capping groups, and linkage to the support are selected so as to allow for selectable cleav- The reagents disclosed herein may be used in conjunction with the method described so as to provide a 5'-phosphate triester blocking group on completed oligonucleotide sequences, as described above. Use of the phosphate triester as a 5'-O-blocking group avoids degradation of complete oligomers by the exonuclease. The 5'-phosphate triester is particularly useful with this method, as it is retained during removal of the capping groups and during exonucleolytic conditions, and, further, is removable without degradation of the oligomer.

The novel reagents thus provide easy functionalization of the terminal 5'-hydroxyl of the olignucleotide chain, provide protection of the chain, and are readily compatible with automated synthesis of nucleic acid sequences. Further, monitoring of the deprotection reaction and thus of the completion of oligonucleotide synthesis can be done accurately via a simple, colorimetric reaction, i.e., the release of the "$R_1$" moiety described above.

It is to be understood that while the invention has been described in conjunction with the preferred specific embodiment thereof, that the foregoing description as well as the examples which follow are intended to illustrate and not limit the scope of the invention, which is defined by the scope of the appended claims. Other aspects, advantages and modifications within the scope of the invention will be apparent to those skilled in the art to which the invention pertains.

EXAMPLE 1

The reagent (2-cyanoethoxy)-2-(2'-4,4-dimethoxytrityloxyethylsulfonyl)ethoxy-N,N-diisopropylaminophosphine (see Formula I) was synthesized as follows.

Commercially available sulfonyldiethanol (65% w/v in $H_2O$) was dried by repeated coevaporation with dry acetonitrile to give a viscous oil which crystallized on standing. To solid sulfonyldiethanol (10.6 g, 68.6 mmole) in pyridine (150 ml) was added 4,4'-dimethoxytrityl chloride (16.95 g, 50 mmole) and the mixture was left stirring in the dark for 18h. The reaction solution was then concentrated in vacuo. The residue dissolved in ethyl acetate (500 ml) was extracted with 5% aq. $NaHCO_3$ and 80% saturated aq. NaCl and the organic phase was dried over anhydrous $Na_2SO_4$. After removal of solvents the product was purified by silica gel column chromatography to give 10.0 g of pure 2-4,4'-dimethoxytrityloxyethylsulfonyl ethanol 1 (TLC, silica in $CH_2Cl_2$; $R_f=0.015$). Chloro-N,N-diisopropylamino-2-cyanoethoxy-phosphine 2 (4.6 mmole) was added rapidly under argon to a stirred solution of 1 (4.6 mmole) and N,N-diisopropylethylamine (DIPEA; 4.6 mmole) in methylene chloride (10 ml) at 0° C.. The solution was allowed to warm to room temperature, diluted with ethyl acetate (50 ml) and washed with 80% saturated aq. NaCl ($2\times20$ ml). The organic phase was dried with anhydrous $Na_2SO_4$ and concentrated by rotary evaporation. The oily product 3 was dissolved in acetonitrile and then aliquoted into 1.5 ml septum-sealed Wheaton vials each containing 100 micromoles of reagent. The solvent was removed by evacuation and the product was stored under argon at $-20°$ C. This crude product was used without further purification.

The dried materials were activated with tetrazole in acetonitrile and coupled to solid-supported oligonucleotides. Subsequently the synthetic DNA was oxidized with aqueous $I_2$ under standard conditions and deprotected with $NH_4OH$ at 60° C. This process gives the 5'-phosphorylated target fragment in quantitative yield. The extent of coupling was determined from the absorption spectrum (498 nm) of an orange solution produced upon treatment of the oligomer with dichloroacetic acid in methylene chloride (5% v/v) prior to deprotection with $NH_4OH$.

EXAMPLE 2

Enzymatic purification of oligonucleo-tides in solution: The fragments 5'-TATCAATTCCAATAAACTTTACTCCAAACC-3' and 5'-AAGGATCCAGTTGGCAGTACAGCCTAGCAGCCATGGAAAC-3' were synthesized on the CPG support (Warner, et al., *DNA* 3, 401 (1984)). The fragments were then 5'-phosphorylated as described in Example 1. The oligomers were removed from the support with $NH_4OH$ at room temperature, then deprotected overnight at 60° C. The solution was evaporated to dryness in a speed-vac concentrator.

The crude product obtained from 2 mg of the support was suspended in 20 micro l of $H_2O$ to which 50 micro l of sodium phosphate buffer, pH 7.0 containing 0.3 units of spleen phosphodiestetase was added. After vortexing the solution was placed at 37° C. for 1 hour.

Polyacrylamide gel analysis revealed that truncated failure sequences were substantially degraded whereas the phosphorylated target fragment was protected from hydrolysis.

EXAMPLE 3

A phosphorylating agent according to Formula III was prepared as follows. The method of Example I was followed through purification of 2-4,4'-dimethoxytrityloxyethylsulfonyl ethanol. Then, chloro-N,N-diisopropylamino-2-cyanoethoxyphosphine oxide (4.6 mmole) was added to a DIPEA solution as described. The product was isolated by precipitation as the barium salt, and used without further purification to phosphorylate a completed oligonucleotide sequence as described in Example 1.

EXAMPLE 4

A phosphitylating agent according to Formula IV is prepared by reaction of 2-4,4'-dimethoxytrityloxyethylsulfonyl ethanol (4.6 mmole) with phosphorous acid (4.6 mmole) in pyridine at about 0° C. The reaction proceeds in the presence of tosyl chloride as an activating agent. The product, 2-4,4'-dimethoxytrityloxyethylsulfonylethoxy phosphate, is isolated, e.g., by precipitation, and coupled to synthetic DNA via a method similar to that described in Example 1 using $(CH_3)_3COCl$ as activating agent. The phosphitylated DNA is oxidized with $I_2$ and deprotected with $NH_4OH$ to give the 5' phosphate. The coupling reaction is monitored as described in Example 1.

EXAMPLE 5

Comparison of chemical phosphorylation with enzymatic: The palindromic BamHI linker sequence GGATCCGGATCC was synthesized on an automated instrument (the Geno-O-Matic) using a solid-supported phosphoramidite chemistry (12). One-half of the support was phosphorylated with reagent 3, detritylated to check the coupling efficiency and fully deprotected. The product was then purified by polyacrylamide gel electrophoresis. The second half of the material was deprotected and purified as the 5'-hydroxyl form which was then 5-phosphorylated with $T_4$ polynucleotide kinase and ATP. The PAGE analyses of $T_4$ DNA ligase reactions using the chemically and enzymatically phosphorylated fragments showed that both sequences were near fully phosphorylated as evidenced by the lack of starting material after ligation.

We claim:

1. A phosphorylating reagent having the structure of Formula I

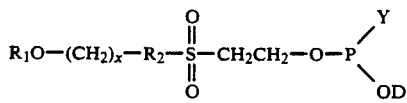

Formula I wherein
(a) R₁ is a colorimetrically detectable species selected from the group consisting of trityloxyacetyl, substituted phenoxyacetyl, unsubstituted phenoxyacetyl, and

wherein the R, R' and R" are independently selected from the group consisting of

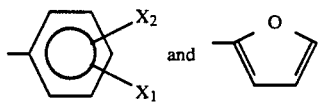

wherein X₁ and X₂ are selected from the group consisting of hydrogen, lower alkyl, lower alkoxy, halogen, nitro, phenyl, sulfonated, amino substituted with from 0 to 2 lower alkyl or lower alkoxy substituents, and carbon atoms which represent part of an aromatic system having from one to five rings;
(b) R₂ is selected from the group consisting of methylene that is mono-substituted with lower alkyl, methylene that is di-substituted with lower alkyl, phenyl, phenyl substituted with lower alkyl, and phenyl substituted with nitro;
(c) Y is selected from the group consisting of amino substituted from 0 to 2 alkyl groups having from 1 to 6 carbon atoms, halogen and trialkylsilyl of from 3 to 12 carbon atoms;
(d) x is an integer in the range of 1 and 50 inclusive; and
(e) D has the structure

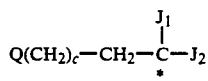

in which J₁ and J₂ are independently selected from the group consisting of hydrogen and alkyl of 1 to 3 carbon atoms, c is 0 or 1, and Q is selected from the group consisting of hydrogen, alkyl of from 1 to 9 carbon atoms, nitro, lower alkylsulfonyl, cyano, p-nitrophenyl, lower alkylthio, arylthio, trihalomethyl, phenyl, β-naphthyl, 9-fluoroenyl and 2-anthraquinonyl, and the * represents the point of attachment to the remainder of the molecule.

2. The phosphorylation reagent of claim 1 wherein x is an integer in the range of 1 to 8 inclusive.

3. The phosphorylation reagent of claim 1 wherein R₁ is 4,4'-dimethoxytrityl.

4. The phosphorylation reagent of claim 1, wherein R₂ is methylene.

5. The phosphorylation reagent of claim 1, wherein D is β-cyanoethyl.

6. The phosphorylation reagent of claim 1, wherein Y is morpholino.

7. The phosphorylation reagent of claim 1, wherein Y is N,N-diisopropylamino.

8. The phosphorylation reagent having the structure of Formula I

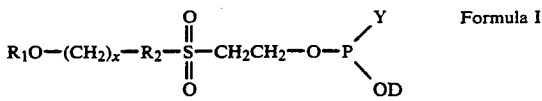

Formula I wherein R₁ is 4,4'-dimethoxytrityl, R₂ is methylene, x is an integer in the range of 1 to 8 inclusive, D is β-cyanoethyl, and Y is morpholino or N-N-diisopropylamino.

9. A phosphorylating reagent having the structure of Formula III

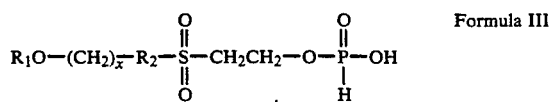

Formula III wherein
(a) R₁ is a colorimetrically detectable species selected from the group consisting of trityloxyacetyl, substituted phenoxyacetyl, unsubstituted phenoxyacetyl, and RR'R"C— wherein the R, R' and R" are independently selected from

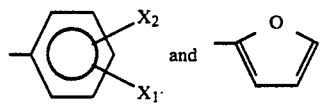

wherein X₁ and X₂ are selected from the group consisting of hydrogen, lower alkyl, lower alkoxy, halogen, nitro, phenyl, sulfonate, amino substituted with from 0 to 2 lower alkyl or lower alkoxy substituents, and carbon atoms which represent part of a polycyclic aromatic system having from one to five rings;
(b) R₂ is selected from the group consisting of methylene, methylene that is mono-substituted with lower alkyl, methylene that is di-substituted with lower alkyl, phenyl, phenyl substituted with lower alkyl, and phenyl substituted with nitro; and
(c) x is an integer in the range of 1 to 50 inclusive.

10. The phosphorylation reagent of claim 9, wherein x is an integer in the range of 1 to 8 inclusive.

11. The phosphorylation reagent of claim 9, wherein R₁ is 4,4'-dimethoxytrityl.

12. The phosphorylating reagent of claim 9, wherein R₂ is methylene.

13. The phosphorylation reagent having the structure of Formula III

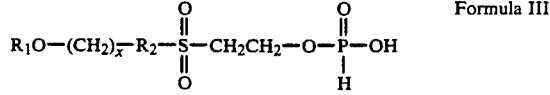

Formula III wherein R₁ is 4,4'-dimethoxytrityl, R₂ is methylene, and x is an integer in the range of 1 to 8 inclusive.

14. A phosphorylating reagent having the structure of Formula IV

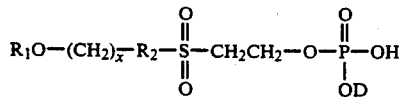 Formula IV wherein
(a) R₁ is a colorimetrically detectable species selected from the group consisting of trityloxyacetyl, substituted phenoxyacetyl, unsubstituted phenoxyacetyl, and

wherein R, R' and R" are independently selected from

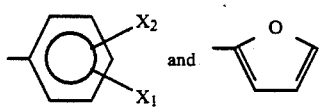

wherein X₁ and X₂ are selected from the group consisting of hydrogen, lower alkyl, lower alkoxy, halogen, nitro, phenyl, sulfonate, amino substituted with from 0 to 2 lower alkyl or lower alkoxy substituents, and carbon atoms which represent part of a polycyclic aromatic system having from one to five rings;
(b) R₂ is selected from the group consisting of methylene, methylene that is mono-substituted with lower alkyl, methylene that is di-substituted with lower alkyl, phenyl, phenyl substituted with lower alkyl, and phenyl substituted with nitro;
(c) x is an integer in the range of 1 to 50 inclusive;
(d) D has the structure

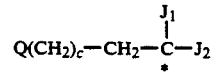

in which J₁ and J₂ are independently selected from the group consisting of hydrogen and alkyl of 1 to 3 carbon atoms, c is 0 or 1, and Q is selected from the group consisting of hydrogen, alkyl of from 1 to 9 carbon atoms, nitro, lower alkylsulfonyl, cyano, p-nitrophenyl, lower alkylthio, arylthio, trihalomethyl, phenyl, β-naphthyl, 9-fluorenyl and 2-anthraquinonyl, and the * represents the point of connection to the remainder of the molecule.

15. The phosphorylation reagent of claim 14, wherein x is an integer in the range of 1 to 8 inclusive.

16. The phosphorylation reagent of claim 14, wherein R₁ is 4,4'-dimethoxytrityl.

17. The phosphorylation reagent of claim 14, wherein R₂ is methylene.

18. The phosphorylation reagent of claim 1, which is (2-cyanoethoxy)-2-(2'-4,4-dimethoxytrityloxyethylsulfonyl)ethoxy-N,N-diisopropyl-aminophosphine.

19. The phosphorylation reagent of claim 9, which is N,N-diisopropylamino-(2-cyanoethoxy)-(2-(2'-(4,4-dimethoxytrityloxy)ethyl-sulfonyl)ethoxy)phosphonate.

20. The phosphorylation reagent of claim 14, which is 2-(4,4'-dimethoxytrityloxy)ethylsulfonylethyloxyphosphate.

* * * * *